US008785416B2

(12) United States Patent
Verges Milano et al.

(10) Patent No.: US 8,785,416 B2
(45) Date of Patent: Jul. 22, 2014

(54) SULPHATED DISACCHARIDES FOR THE TREATMENT OF NEURODEGENERATIVE AND/OR NEUROVASCULAR DISEASES

(75) Inventors: Josep Verges Milano, Barcelona (ES); Antonio Garcia Garcia, Alpedrete (ES); Ramon Ruhi Roura, Barcelona (ES); Eulalia Montell Bonaventura, Sant Quirze Del Valles (ES); Manuela Garcia Lopez, Madrid (ES); Carlos Raul Alaez Verson, Blanes (ES); Josep Escaich Ferrer, Barcelona (ES); Javier Egea Maiquez, Madrid (ES); Pilar Negredo Madrigal, Madrid (ES); Silvia Lorrio Gonzalez, Alcobendas (ES)

(73) Assignees: Bioiberica, S.A., Barcelona (ES); Universidad Autonoma de Madrid, Madrid (ES)

( * ) Notice: Subject to any disclaimer, the term of this patent is extended or adjusted under 35 U.S.C. 154(b) by 2 days.

(21) Appl. No.: 13/520,069

(22) PCT Filed: Dec. 22, 2010

(86) PCT No.: PCT/EP2010/070613
§ 371 (c)(1),
(2), (4) Date: Aug. 17, 2012

(87) PCT Pub. No.: WO2011/080203
PCT Pub. Date: Jul. 7, 2011

(65) Prior Publication Data
US 2012/0309707 A1    Dec. 6, 2012

(30) Foreign Application Priority Data
Dec. 29, 2009 (ES) .................................. 200902399

(51) Int. Cl.
*A61K 31/7016* (2006.01)
*A61K 31/715* (2006.01)
*C07H 3/04* (2006.01)
*C07H 5/06* (2006.01)

(52) U.S. Cl.
USPC .................. 514/53; 514/54; 514/25; 536/54; 536/123.13; 536/123.1; 536/4.1; 536/118

(58) Field of Classification Search
USPC .......... 514/53, 54, 25; 536/54, 123.13, 123.1, 536/4.1, 118
See application file for complete search history.

(56) References Cited

FOREIGN PATENT DOCUMENTS

| EP | 1300411 A1 | 4/2003 |
|---|---|---|
| WO | 98/55514 A1 | 12/1998 |
| WO | 2005/025502 A2 | 3/2005 |
| WO | 2005/076743 A2 | 8/2005 |
| WO | 2008/151898 A1 | 12/2008 |

OTHER PUBLICATIONS

Merck Manual of Diagnosis and Therapy (17th ED) (1999), p. 1358, 1376-1377.*
International Search Report for PCT/EP2010/070613 dated Mar. 16, 2011.

* cited by examiner

*Primary Examiner* — Shaojia Anna Jiang
*Assistant Examiner* — Michael C Henry
(74) *Attorney, Agent, or Firm* — Sughrue Mion, PLLC (57) ABSTRACT

The present invention relates to the use of a series of sulphated disaccharides for the preparation of a medicament for the treatment or prevention of a neurodegenerative and/or neurovascular disease, of a traumatic brain injury or of a traumatic spinal cord injury. The present invention also relates to the use of said sulphated disaccharides for the preparation of a neuroprotective medicament or of an antioxidant medicament. The neurodegenerative and/or neurovascular diseases are preferably: Alzheimer's disease, Parkinson's disease, amyotrophic lateral sclerosis and stroke.

17 Claims, 4 Drawing Sheets

SULPHATED DISACCHARIDES FOR THE TREATMENT OF NEURODEGENERATIVE AND/OR NEUROVASCULAR DISEASES

CROSS REFERENCE TO RELATED APPLICATIONS

This application is a National Stage of International Application No. PCT/EP2010/070613 filed Dec. 22, 2010, claiming priority based on Spanish Patent Application No. 200902399, filed Dec. 29, 2009, the contents of all of which are incorporated herein by reference in their entirety.

TECHNICAL FIELD OF THE INVENTION

The present invention relates to the use of a series of sulphated disaccharides for the preparation of a medicament for the treatment of a neurodegenerative and/or neurovascular disease, as well as for the treatment of a traumatic brain or spinal cord injury. The present invention also relates to the use of said sulphated disaccharides for the preparation of a neuroprotective medicament.

BACKGROUND OF THE INVENTION

Neurodegenerative diseases, neurovascular diseases and traumatic brain and spinal cord injuries are one of the most important causes of disability and death in the population. Alzheimer's disease, Parkinson's disease, amyotrophic lateral sclerosis and stroke stand out among these diseases.

These diseases are generally characterized by a loss of neurons, which translates into the onset of language and memory disorders in Alzheimer's disease, movement coordination disorders in Parkinson's disease, paralysis of the voluntary muscles involved in motility, speech and respiration in amyotrophic lateral sclerosis (ALS), hemiplegias and sensory losses in stroke and paralysis in traumatic brain and spinal cord injuries.

Oxidative cell stress is involved in various neurodegenerative and neurovascular diseases. The central nervous system, and specifically the brain, has a high oxygen requirement. Oxygen consumption leads to the overproduction of so-called reactive oxygen species (ROS), such as superoxide or hydroxyl type free radicals or non-radical oxygen such as hydrogen peroxide ($H_2O_2$), which cause damage both in neuronal and in vascular cells (*Oxidative neurotoxicity in rat cerebral cortex neurons: synergistic effects of $H_2O_2$ and NO on apoptosis involving activation of p38 mitogen-activated protein kinase and caspase-3*, J. Y. Wang et al., *J. Neurosci. Res.* 72, 508-519 (2003)). To control the levels of these oxidant compounds, cells have antioxidant systems, such as superoxide dismutase, glutathione peroxidase, transferrin or vitamin E. Under normal physiological conditions there is an equilibrium between these antioxidant systems and reactive oxygen species. However, problems may arise when said equilibrium is altered due to a decrease of the antioxidant defenses and/or to an overproduction of reactive oxygen species. Under those conditions, oxidative stress can cause cell damage and subsequent cell death, neurons being particularly vulnerable cells.

It is known that oxidative stress is one of the main cell death mechanisms in different cytotoxic models, such as that of glutamate (*Glutamate induces oxidative stress and apoptosis in cerebral vascular endothelial cells: contributions of HO-1 and HO-2 to cytoprotection*, H. Parfenova et al., *Am. J. Physiol.* 290: C1399-C1410 (2006)) or in the $H_2O_2$-induced cytotoxicity model (*Distinct protective mechanisms of HO-1 and HO-2 against hydroperoxide-induced cytotoxicity*, Y. S. Kim et al., *Free Radic. Biol. Med.* 38, 85-92 (2005)) and in neurodegenerative and neurovascular diseases such as Alzheimer's disease, Parkinson's disease, amyotrophic lateral sclerosis, stroke and arteriosclerosis (*Oxidative stress in brain aging, neurodegenerative and vascular diseases: an overview*, E. Mariani et al., *J. Chromatogr. B Analyt. Technol. Biomed. Life Sci.* 827, 65-75 (2005); *Oxidative stress and neuronal death/survival signaling in cerebral ischemia*, A. Saito et al., *Mol. Neurobiol.* 31, 105-116 (2005); *Oxidative stress in the context of acute cerebrovascular stroke*, M. M. H. El Kossi et al., *Stroke* 31, 1889-1892 (2000); *The oxidant stress hypothesis of atherogenesis*, L. Iuliano, *Lipids* 36, suppl: S41-44 (2001)).

The compounds of the present invention are disaccharides containing one or more sulphate groups in their structure, first described in patent EP 1300411 (U.S. Pat. No. 6,680,304). They are useful in the treatment of arthrosis (patent EP 1300411) and in the treatment of tendon, ligament and bone diseases (patent application WO 2008/151898).

The basic structure of these compounds contains the monosaccharides glucuronic acid and glucosamine, bonded by means of $\beta$-(1→3) bonds, and with a sulphate group in C-4 and/or in C-6 of the monosaccharide glucosamine.

In view of the above, it is of great interest to find drugs capable of protecting neurons under oxidative stress conditions and of reducing the generation of reactive oxygen species. Said drugs could be highly useful as therapeutic tools for the treatment of neurodegenerative and/or neurovascular diseases, as well as for the treatment of traumatic brain or spinal cord injuries.

The use of the sulphated disaccharides of the present invention in the treatment of a neurodegenerative disease and/or of a neurovascular disease as well as in the treatment of a traumatic brain or spinal cord injury has not been described up until now.

DISCLOSURE OF THE INVENTION

The present inventors have surprisingly found that the compounds described in patent EP 1300411, defined by formula (I), reduce the formation of reactive oxygen species and have neuroprotective activity, protecting against cell death induced by oxidative stress, or by oxygen and glucose deprivation. These compounds also have neuroprotective activity in an in vivo cerebral infarction or stroke model. Furthermore, said compounds do not have cell toxicity and reduce the release of inflammatory markers by astrocytes. The compounds of formula (I) can therefore be used in the treatment of neurodegenerative and/or neurovascular diseases, of a traumatic brain injury or of a traumatic spinal cord injury, and also as neuroprotectors.

The present inventors have also found that the process for obtaining the disulphated disaccharide Ic described in the present invention has the advantage of obtaining said compound with a higher yield with respect to the process previously described in patent EP 1300411.

Thus, the present invention relates to the use of a compound of formula (I):

(I)

or a pharmaceutically acceptable salt, prodrug or solvate thereof,
wherein:
$R^1$ is selected from hydrogen, linear or branched $C_1$-$C_4$ alkyl, phenylalkyl of less than ten carbon atoms and —$COCH_3$;
$R^2$ is selected from hydrogen, —$COCH_3$ and —$SO_3Y$;
$R^3$ is selected from hydrogen, linear or branched $C_1$-$C_4$ alkyl, phenylalkyl of less than ten carbon atoms, —$COCH_3$ and —COPh, wherein Ph is phenyl;
G is selected from —$COOR^4$ and —COOY;
A and B are independently selected from hydrogen, —$SO_3H$, —$SO_3Y$ and —$COCH_3$,
wherein either A or B is necessarily either —$SO_3H$ or —$SO_3Y$;
$R^4$ is selected from hydrogen, $C_1$—$O_2$ alkyl and arylalkyl of less than sixteen carbon atoms,
Y is an organic or inorganic cation,
for the preparation of a medicament for the treatment or prevention of a neurodegenerative and/or neurovascular disease, of a traumatic brain injury or of a traumatic spinal cord injury in a mammal, especially in humans.

In a preferred embodiment, the compounds of formula (I) are those wherein $R^1$ is selected from hydrogen and linear $C_1$-$C_4$ alkyl and G is selected from —$COOR^4$ and —COOY, wherein $R^4$ is hydrogen or $C_1$-$C_2$ alkyl and Y is an inorganic cation.

In a more preferred embodiment, the compounds of formula (I) are those wherein: $R^1$ is hydrogen, $R^2$ is —$COCH_3$ and $R^3$ is hydrogen. The compounds of formula (I) wherein $R^1$ is methyl, $R^2$ is —$COCH_3$ and $R^3$ is hydrogen are likewise preferred.

In a particularly preferred embodiment, the compounds of formula (I) are those wherein: A is hydrogen, B is —$SO_3Y$ and G is —COOY, wherein Y is an inorganic cation. The compounds of formula (I) wherein: A is —$SO_3Y$, B is hydrogen and G is —COOY, wherein Y is an inorganic cation, are also particularly preferred. The compounds of formula (I) wherein: A and B are —$SO_3Y$ and G is —COOY, wherein Y is an inorganic cation, are likewise particularly preferred.

An especially preferred individual compound of the invention is: methyl 2-acetamido-2-deoxy-3-O-(β-D-glucopyranosyluronic acid)-4-O-sulpho-α-D-glucopyranoside, disodium salt, of formula:

Another especially preferred individual compound of the invention is: methyl 2-acetamido-2-deoxy-3-O-(β-D-glucopyranosyluronic acid)-6-O-sulpho-α-D-glucopyranoside, disodium salt, of formula:

Another especially preferred individual compound of the invention is: methyl 2-acetamido-2-deoxy-3-O-(β-D-glucopyranosyluronic acid)-4,6-di-O-sulpho-α-D-glucopyranoside, trisodium salt, of formula:

In another preferred embodiment, the neurodegenerative and/or neurovascular disease is associated with oxidative stress.

In another also preferred embodiment, the neurodegenerative and/or neurovascular disease is associated with neuroinflammation.

In another also preferred embodiment, the medicament is an antioxidant medicament.

In another also preferred embodiment, the medicament is a neuroprotective and/or neuroreparative medicament.

In another also preferred embodiment, the medicament is a medicament for promoting neurogenesis, the emission of neurites or neuronal plasticity in the treatment or prevention of a neurodegenerative and/or neurovascular disease, of a traumatic brain injury or of a traumatic spinal cord injury.

In another also preferred embodiment, the treatment or prevention results in the treatment or prevention of neuroinflammation associated with a neurodegenerative or neurovascular disease.

The treatment or prevention preferably results in the treatment of prevention of a neurodegenerative and/or neurovascular disease selected from the group consisting of Alzheimer's disease, Parkinson's disease, amyotrophic lateral sclerosis, multiple sclerosis, stroke, transient ischemic brain attack, Huntington's disease, Friedreich's ataxia, spongiform encephalopathies, dementia with Lewy bodies, Pick's disease, mild cognitive impairment, epilepsy, migraine, schizophrenia, bipolar disorder, vascular dementia and arteriosclerosis. From among these diseases, the most preferred are: Alzheimer's disease, Parkinson's disease, amyotrophic lateral sclerosis and stroke.

The treatment or prevention preferably results in the treatment or prevention of a traumatic brain or spinal cord injury.

The present invention also relates to the use of a compound of formula (I) defined above, or a pharmaceutically acceptable salt, prodrug or solvate thereof, for the preparation of a neuroprotective and/or neuroreparative medicament.

The present invention also relates to the use of a compound of formula (I) defined above, or a pharmaceutically acceptable salt, prodrug or solvate thereof, for the preparation of an antioxidant medicament, preferably useful in the treatment of age-related macular degeneration.

Likewise, the present invention also relates to the use of a compound of formula (I) defined above for the preparation of a medicament for the treatment or prevention of a disease caused by oxidative stress, of a disease requiring neuroprotection or of a disease requiring neurogenesis in a mammal.

The medicament is preferably suitable for oral or topical administration or is presented in injectable form.

The present invention also relates to the use of a compound of formula (I) defined above in the preparation of a reagent for biological assays of oxidative stress in cells or of oxygen and glucose deprivation in tissues.

The present invention also relates to a process for the preparation of the compound of formula (Ic), (Ic)

characterized in that it comprises the following stages:
(a) reacting the compound of formula (Va)

(Va)

with the $SO_3$.pyridine complex;
(b) treating the intermediate compound obtained in stage (a) with sodium hydroxide;
(c) purifying by precipitation in water/isopropyl alcohol; and
(d) in the event that after stage (c) the compound of formula (Ic) still contains salts, optionally purifying it by column chromatography.

The present invention also relates to a compound represented by formula (I) defined above, or a pharmaceutically acceptable salt, prodrug or solvate thereof, for use in the treatment or prevention of a neurodegenerative and/or neurovascular disease, of a traumatic brain injury or of a traumatic spinal cord injury. The neurodegenerative and/or neurovascular disease is preferably selected from the group consisting of Alzheimer's disease, Parkinson's disease, amyotrophic lateral sclerosis, multiple sclerosis, stroke, transient ischemic brain attack, Huntington's disease, Friedreich's ataxia, spongiform encephalopathies, dementia with Lewy bodies, Pick's disease, mild cognitive impairment, epilepsy, migraine, schizophrenia, bipolar disorder, vascular dementia and arteriosclerosis.

Likewise, the present invention also relates to a compound represented by formula (I) defined above, or a pharmaceutically acceptable salt, prodrug or solvate thereof, for use as a neuroprotector and/or antioxidant.

The compounds of formula (I) used in the present invention have an anomeric carbon in their structure, so the anomeric forms α and β, as well as mixtures thereof, are included in the present invention.

The compounds of formula (I) of the present invention can be in crystalline form as free compounds or as solvates. Suitable solvates are pharmaceutically acceptable solvates. The solvate is preferably a hydrate.

The compounds of formula (I) of the present invention have purity levels as active ingredients greater than 70%, preferably greater than 95%.

The preparation of the compounds of formula (I), according to the present invention, can be carried out following the synthetic routes described in patent EP 1300411.

Depending on the nature of cation Y (organic or inorganic, and among the latter preferably metal cations), organic or inorganic salts can be obtained. Examples of inorganic salts include sodium, potassium, calcium, magnesium, aluminium, ammonium and lithium salts, for example. Examples of organic salts include, ethanolamine, triethanolamine and basic amino acid salts, for example.

Furthermore, the present invention describes an improved process in a pilot plant for obtaining compound Ic from the intermediate compound Va, since a drawback of the process described above for that synthetic stage was the low yield.

(intermediate compound Va)

(compound Ic)

From the intermediate compound Va, which can be prepared by means of the process described in patent EP 1300411, the two sulphate groups are introduced using the $SO_3$.pyridine complex and, without isolating the intermediate formed, the removal of the pivaloyl protecting groups is carried out to obtain compound Ic. The purification of the compound Ic is carried out by precipitation followed, if desired, by a column chromatography.

The modifications introduced in the preparation of compound Ic from Va, with respect to the process described in patent EP 1300411, are the following:
use of the sulphur trioxide-pyridine ($SO_3$.pyridine) complex in the presence of pyridine as a solvent, instead of using the sulphur trioxide-trimethylamine ($SO_3.NMe_3$) complex in N,N-dimethylformamide;
elimination of a stage in the synthetic process, since the intermediate with the two sulphate groups and the pivaloyl protecting groups is not isolated; and
purification of the product by precipitation with water/isopropyl alcohol mixtures.

With these modifications in the process for obtaining compound Ic from intermediate compound Va, a 31% yield was obtained instead of the 13.8% yield described above (two synthesis steps).

When a prodrug is mentioned in the present invention it refers to those derivatives which, in vivo, become the compounds of the present invention. Those prodrugs which increase the bioavailability of the compounds of the present invention when they are administered to a patient, or which increase the release of the compound of formula (I) in the brain, for example, are preferred.

When a neuroprotective medicament is mentioned in the present invention it refers to a medicament for protecting vulnerable neurons in neurodegenerative, neurovascular diseases and in traumatic brain and spinal cord injuries.

When a neuroreparative medicament is mentioned in the present invention it refers to a medicament for repairing damaged neurons in neurodegenerative, neurovascular diseases and in traumatic brain and spinal cord injuries.

When neurogenesis is mentioned in the present invention it refers to the formation of new neurons and new neurites and interneuronal connections.

When an antioxidant medicament is mentioned in the present invention it refers to an anti-reactive oxygen species or anti-free radical medicament.

When neuroinflammation is mentioned in the present invention it refers to the astrogliosis presented in the nervous system of patients with neurodegenerative and/or neurovascular diseases or with traumatic brain or spinal cord injuries.

For using in the treatment or prevention of a neurodegenerative disease, of a neurovascular disease, of a traumatic brain injury, of a traumatic spinal cord injury, of a disease caused by oxidative stress, of a disease requiring neuroprotection or neurogenesis, in the treatment or prevention of neuroinflammation associated with a neurodegenerative or neurovascular disease, as an antioxidant medicament or as a neuroprotective and/or neuroreparative medicament, the compounds of formula (I) are formulated in suitable pharmaceutical compositions, using conventional techniques and excipients or carriers, such as those described in Remington: The Science and Practice of Pharmacy 2000, edited by Lippincott Williams and Wilkins, 20th edition, Philadelphia. The pharmaceutical compositions comprise at least one compound of formula (I) of the present invention, or a pharmaceutically acceptable salt, prodrug or solvate thereof with a pharmaceutically acceptable carrier for the administration to the patient. Said pharmaceutical compositions can be administered to the patient in required doses. The administration of the pharmaceutical compositions can be carried out through different routes, for example, oral, intravenous, intraperitoneal, intralesional, perilesional, intratendinous, peritendinous, intrathecal, subcutaneous, intramuscular, topical, sublingual, transdermal or intranasal route. The pharmaceutical compositions of the invention include a therapeutically effective amount of active compound of formula (I), said amount depending on many factors, such as for example the physical condition of the patient, age, sex, particular compound to be used, administration route, administration frequency or severity of the disease. Furthermore, it will be understood that said dosage of active compound of formula (I) can be administered in single or multiple dose units to provide the desired therapeutic effects.

The pharmaceutical preparations of the invention will generally be in solid form, liquid form or as a gel. The pharmaceutical preparations in solid form that can be prepared according to the present invention include powders, pellets, microspheres, nanoparticles, tablets, dispersible granules, capsules, seals and suppositories. The preparations in liquid form include solutions, suspensions, emulsions, syrups and elixirs. The preparations in solid form which are to be converted, immediately before being used, into preparations in liquid form are also contemplated. Said liquid forms include solutions, suspensions and emulsions.

In the figures and examples described below, compound Ic is:

And compound Ib is:

DETAILED DESCRIPTION OF THE PREFERRED EMBODIMENTS

The following examples are merely illustrative and do not represent a limitation of the scope of the present invention.

Examples

Example 1

Improved process for the preparation of methyl 2-acetamido-2-deoxy-3-O-(β-D-glucopyranosyluronic acid)-4,6-di-O-sulpho-α-D-glucopyranoside, trisodium salt, (compound Ic) from intermediate compound Va (intermediate compound Va)

(compound Ic)

4.7 L of pyridine were introduced in a dry reactor under a slight nitrogen stream and at room temperature. 900 g (1.475 moles) of methyl 2-acetamido-2-deoxy-3-O-(methyl 2,3,4-tri-O-pivaloyl-β-D-glucopyranosyluronate)-α-D-glucopyranoside (intermediate compound Va) and 864 g (6.031 moles) of the $SO_3$.pyridine complex were added. The mixture was heated at 40° C. for 5 hours with stirring. Then, it was cooled at 20° C., 0.9 L of water were added and a solution of 216 g of sodium hydroxide in 5.4 L of water was slowly added for 30 minutes, cooling at 15-20° C. Then, it was distilled under vacuum to dryness, and the pyridine remains were removed by adding water and distilling under vacuum without exceeding a temperature of 55° C. The resulting residue was dispersed in 3.8 L of methanol and 0.9 L of water and cooled at 0° C., then adding a solution of 324 g of sodium hydroxide in 2.7 L of water for 30 minutes and at 0° C. The temperature was allowed to reach 20° C., it was heated at 40° C. for 2 hours, and subsequently left at room temperature with stirring overnight. Then, 99 mL of glacial acetic acid were added until pH 8 and most of the solvent was distilled under vacuum, without exceeding a temperature of 55° C. Then, and under stirring, 9 L of isopropyl alcohol were added. The mixture was heated at 55° C. for 15 minutes and cooled at room temperature. After stirring for 2 hours, it was filtered in a Büchner funnel to obtain, after drying, 875 g of product containing compound Ic and salts. Compound Ic was purified by means of precipitation to remove the salts. To that end, 875 g of reaction product were dissolved in 1,800 mL of deionized water, heating at 45-50° C. Subsequently, 900 mL of isopropyl alcohol were added, it was slowly cooled at room temperature, and it was left at this temperature and under stirring for one hour. After that time, it was cooled at 0-5° C. for 2 hours, the solid formed, made up of salts, was filtered, washing with a cold solution of water-isopropyl alcohol (2:1). The mother liquor obtained was precipitated by adding isopropyl alcohol with vigorous stirring which was maintained for 2 hours, a product which still contained salts being obtained after filtering and drying the solid at 40° C. in the vacuum oven. The precipitation was repeated again, 271 g of product with a low salt content being obtained. Finally, purification was carried out by means of chromatography in a Dowex 50WX2 column (200-400 mesh) in calcium form (eluent: water), 265 g (31% yield) of pure Ic being obtained.

Optical Rotation: $[\alpha]_D$+18.5° (c 0.54, $H_2O$). It was obtained at λ=589 nm, 20° C. and a 10 cm cell with a capacity for 1 mL.

MS: calculated for $C_{15}H_{22}NO_{18}S_2Na_2$: 614.4. Found: m/z 613.7 [M$^-$-Na].

$^1$H-NMR spectrum-(400 MHz, $D_2O$): δ ppm 4.76 (d, 1H, $J_{12}$=3.6 Hz, H-1), 4.60 (d, 1H, $J_{12}$=7.6 Hz, H-1'), 4.52-4.58 (m, 1H, H-6a), 4.36 (dd, 1H, $J_{34}$=10.0 Hz, $J_{32}$=8.8 Hz, H-3), 4.26-4.29 (m, 4H, H-4, H-2, H-6b, H-5), 3.64-3.69 (m, 1H, H-5'), 3.56 (m, 1H, H-4'), 3.37-3.49 (5H, H-3', $OCH_3$, H-2'), 2.03 (s, 3H, $COOCH_3$).

$^{13}$C-NMR spectrum (100 MHz, $D_2O$): δ ppm 176.61, 174.93 (2×C, COONa, $COOCH_3$), 101.77 (C-1'), 98.46

(C-1), 77.63 (C-5'), 76.22 (C-3'), 75.97 (C-4), 73.41 (C-2'), 73.23 (C-3), 72.52 (C-4'), 69.59 (C-5), 68.29 (C-6), 56.07 (OCH$_3$), 53.91 (C-2), 22.84 (COOCH$_3$).

The NMR spectra were recorded in a 400 MHz Varian instrument. All the assignments were made using standard $^1$H-$^1$H-COSY and HMQC (Heteronuclear Multiple Quantum Coherence) experiments.

Example 2

Toxicity Studies

The cell toxicity studies were performed on the SH-SY5Y human neuroblastoma cell line, incubating said cells for 48 hours with the compound under study. The cell viability was assessed by quantifying the release of lactate dehydrogenase (LDH), which is a cytoplasmic enzyme which is released into the extracellular medium when the integrity of the cytoplasmic membrane is lost. Compounds Ic and Ib did not show toxicity at the 100 µM dose.

Example 3

Neuroprotective Effect of the Compounds of Formula (I) Against Cell Death Induced by Oxidative Stress It is known that oxidative stress is involved in neurodegenerative and neurovascular diseases, therefore the objective was to determine the neuroprotective effect of the compounds of formula (I) when the SH-SY5Y human neuroblastoma cells are exposed to oxidative stress.

An oxidative stress model consists of blocking mitochondrial respiratory chain complexes I and V by means of the combination of rotenone plus oligomycin-A, respectively. As a result of the interruption of the mitochondrial respiratory chain, the cell is unable to continue producing ATP, and the free radicals are generated exceeding the capacity of the cell to neutralize them, and as a result, cell death occurs.

Furthermore, for comparison purposes, the neuroprotective effect of chondroitin sulphate (CS), a sulphated glycosaminoglycan with a polymeric structure characterized by a disaccharide which is repeated, made up of N-acetylgalactosamine and D-glucuronic acid, was determined. Most of the N-acetylgalactosamine units are sulphated. The chondroitin sulphate used in the assay of the present invention was mostly a mixture of 4-chondroitin sulphate and 6-chondroitin sulphate. It is known that chondroitin sulphate protects neurons against damage induced by glutamate (*A protective action of chondroitin sulfate proteoglycans against neuronal cell death induced by glutamate*, Okamoto et al., Brain Res. 637, 57-67 (1994)), as well as that chondroitin sulphate protects SH-SY5Y human neuroblastoma cells subjected to oxidative stress (*Chondroitin sulfate protects SH-SY5Y cells from oxidative stress by inducing heme oxigenase-1 via phosphatidylinositol 3-kinase/Akt*, (N. Cañas et al., J. Pharmacol. Exp. Ther. 323(3), 946-953 (2007)).

Finally, the effect of the trolox (a component of vitamin E with antioxidant activity) in the same oxidative stress model was also determined for comparison purposes.

Materials and Methods

SH-SY5Y human neuroblastoma cells were cultured in a monolayer in 75 cm$^2$ flasks with a vented stopper. The culture medium used was Dulbecco's Modified Eagle's Medium (DMEM) with a high glucose content (4.5 mg/L) and supplemented with 10% foetal bovine serum, 2 mM L-Glutamine, 50 IU/mL penicillin and 50 µg/mL streptomycin.

The cell cultures were maintained in an incubator at 37° C. in a humid environment, with 5% CO$_2$ and 95% air. The culture medium was changed twice a week, performing 1:4 passages when the cells reached 70-80% confluence. To perform the passages, the cells were detached by means of their treatment with trypsin-EDTA.

For the cell viability assays, the cells were seeded in sterile 48-well plates at a density of 80,000 cells/well. The experiments were performed 24-48 hours after their seeding.

To evaluate the neuroprotective effect of the compounds, the SH-SY5Y cells were preincubated for 24 hours with the compound under study, and subsequently incubated for 24 hours with the compound under study in the presence of the toxic substances (a combination of 10 µM rotenone and 1 µM oligomycin-A); at the end of this period the cell viability was evaluated by quantifying the release of the LDH enzyme.

The assessment of this enzyme was performed by means of a commercial kit (Cytotoxicity detection kit-LDH; Roche) following the instructions of the company. The samples were colorimetrically analyzed in a plate reader (Labsystems iEMS Reader MF), using the suitable filter at 490-600 nm and obtaining the absorbance values.

The % of cell death was defined as the % of LDH released into the extracellular medium with respect to the total (sum of intra- and extracellular LDH).

Compounds Ic and Ib were studied at four concentrations (0.001, 0.003, 0.01 and 0.03 µM), chondroitin sulphate (supplied by Bioibérica, S.A.) was assayed at two concentrations (10 and 60 µM) and trolox (Sigma Aldrich) was assayed at two concentrations (30 and 300 µM). The experiment also included the baseline (SH-SY5Y cells in the absence of compound and of toxic stimulus) and the control (SH-SY5Y cells cultured in the absence of compound and in the presence of the toxic stimulus rotenone plus oligomycin).

Results

Figure 1:
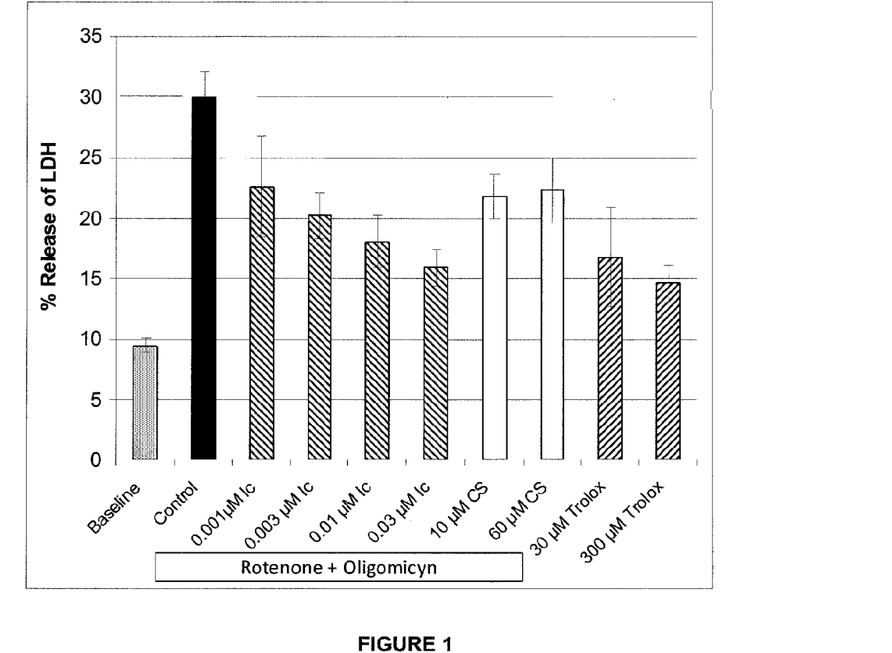
FIG. 1 depicts, at four concentrations (0.001, 0.003, 0.01, and 0.03 μM), the effect of compound Ic on the release of LDH (lactate dehydrogenase) into the extracellular medium as an indicator of cell death induced by the combination of rotenone and oligomycin as a toxic stimulus. The effect of compound Ic was compared with the effect of chondroitin sulphate (CS) at two concentrations (10 and 60 μM) and with the effect exerted by trolox at two concentrations (30 and 300 μM). The baseline (SH-SY5Y cells in the absence of compound Ic and of toxic stimulus) and the control (SH-SY5Y cells cultured in the absence of compound Ic and in the presence of rotenone+oligomycin) are also included.
Figure 2:
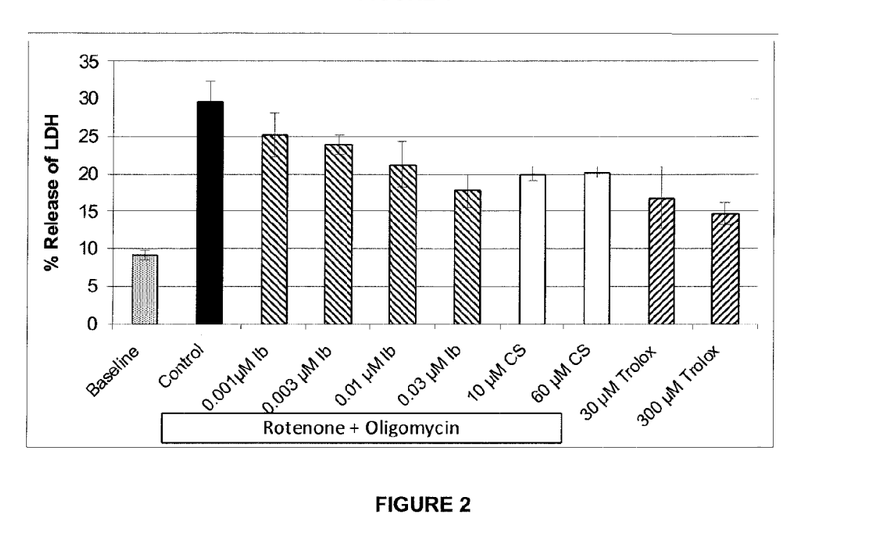
FIG. 2 depicts, at four concentrations (0.001, 0.003, 0.01 and 0.03 μM), the effect of compound Ib on the release of LDH into the extracellular medium as an indicator of cell death induced by the combination of rotenone and oligomycin as a toxic stimulus. The effect of compound Ib was compared with the effect of chondroitin sulphate at two concentrations (10 and 60 μM) and with the effect exerted by trolox at two concentrations (30 and 300 μM). The baseline (SH-SY5Y cells in the absence of compound Ib and of toxic stimulus) and the control (SH-SY5Y cells cultured in the absence of compound Ib and in the presence of rotenone+oligomycin) are also included.

FIGS. 1 and 2 show the results of neuroprotection of compounds Ic and Ib against cell death (% of released LDH) induced by the combination of rotenone and oligomycin. Said figures also show the comparative results of chondroitin sulphate and of trolox.

Compound Ic (FIG. 1) achieved the maximum statistically significant protection (47%) at the concentration of 0.03 µM.

Compound Ib (FIG. 2) also achieved the maximum statistically significant protection at the concentration of 0.03 µM, although in this case the protection was of 40%.

As can be observed in FIGS. 1 and 2, compounds Ic and Ib were more effective than chondroitin sulphate and than trolox in terms of their protective effects, although chondroitin sulphate and trolox reduced cell death induced by rotenone and oligomycin, this protective effect was detected at substantially higher concentrations (10 and 60 µM for chondroitin sulphate; 30 and 300 µM for trolox) than the concentrations required for compounds Ic and Ib.

Example 4

Effect of the Compounds of Formula (I) on the Generation of Reactive Oxygen Species (ROS)

The overproduction of ROS leads to damages both in neuronal cells and in the vascular endothelium, due to the destruction of the lipid membrane and to the rupture of DNA.

The objective was to determine the capacity of the compounds of formula (I) to reduce the generation of ROS after exposing the cells to hydrogen peroxide.

Hydrogen peroxide was used as a producer of free radicals for the purpose of inducing a cell lesion by oxidative stress.

To determine the production of free radicals, the fluorescent probe 2"-7"-dichlorodihydrofluorescein diacetate (DCFDA) was used, which is sensitive to the presence of free radicals, such that when the latter are intracellularly generated there is an increase of fluorescence.

When the fluorescent probe passes into the cell, intracellular esterases hydrolyze the probe, transforming it into $DCFH_2$. Peroxidases, cytochrome C and $Fe^{2+}$ can oxidize the probe to DCF in the presence of hydrogen peroxide, and the accumulation of DCF in the cell can be measured as an increase of fluorescence at 530 nm when it is excited at 485 nm.

Materials and Methods

SH-SY5Y human neuroblastoma cells were cultured following the procedure described in Example 3.

For the fluorescence assays, the cells were seeded in 96-well plates with opaque walls at a density of 10,000 cells/well. The experiments were performed 24-48 hours after the seeding.

To evaluate the effects of compound Ic on the generation of ROS, the cells were incubated with increasing concentrations of compound Ic (0.01 and 0.1 µM) for 24 hours and then they were preincubated with the fluorescent probe DCFDA for 45 minutes. Subsequently, the baseline fluorescence of each well, both of the wells containing cells and compound Ic and of those containing only the cells, was quantified. Then, hydrogen peroxide was added at the concentration of 50 µM, both to the wells containing cells and compound Ic and to those containing only the cells, and the fluorescence of DCFDA was assessed as an indicator of the generation of ROS at 30 and 60 minutes after the addition of hydrogen peroxide. The baseline fluorescence of each well containing compound Ic was subtracted from it in order to obtain the net fluorescence. The fluorescence values were standardized with respect to the fluorescence caused by hydrogen peroxide at 30 minutes (this value was considered to be 1).

The baseline of the assay (cells in the absence of compound and of toxic stimulus) and the control (cells in the absence of compound and in the presence of hydrogen peroxide) were also included in the study.

Results

Figure 3:
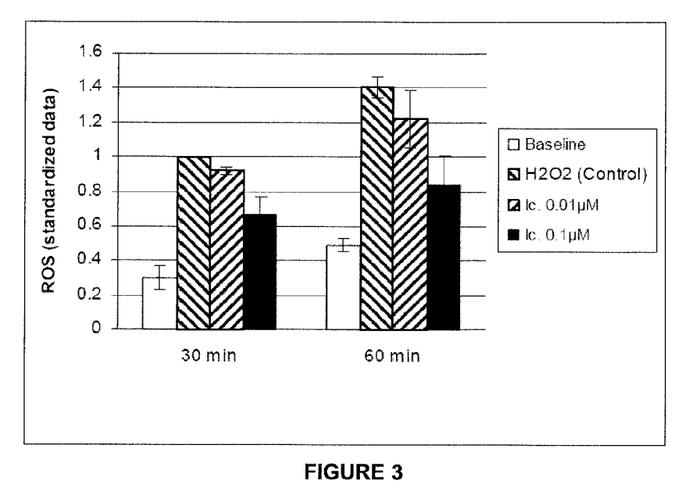
FIG. 3 depicts, at two concentrations (0.01 and 0.1 μM), the effect of compound Ic on the generation of intracellular reactive oxygen species (ROS) at 30 and 60 minutes after exposing the SH-SY5Y cells (incubated with compound Ic) to hydrogen peroxide ($H_2O_2$). The baseline (cells in the absence of compound Ic and of $H_2O_2$) and the control (cells in the absence of compound Ic and with $H_2O_2$) are also included.

FIG. 3 shows that the addition of hydrogen peroxide to the SH-SY5Y cells tripled the production of ROS at 30 and 60 minutes of incubation (Control bars of the Figure).

When the cells were treated for 24 hours with compound Ic, before the exposure to hydrogen peroxide, the ROS generated by hydrogen peroxide at 30 and 60 minutes were significantly reduced. When compound Ic was present in the cells at the concentration of 0.1 µM, a statistically significant reduction of 40% in the formation of free radicals induced by hydrogen peroxide was observed.

These results indicate that the compounds of the present invention are capable of reducing the formation of radical species, with the consequent neuroprotective and antioxidant effect, which makes the compounds of the present invention potential drugs for the treatment of diseases associated with oxidative stress, such as neurodegenerative and neurovascular diseases.

Example 5

Neuroprotective Effect of the Compounds of Formula (I) in Hippocampal Slices Subjected to Oxygen and Glucose Deprivation (OGD)

A known in vitro brain ischemia model consists of oxygen and glucose deprivation in rat hippocampal slices (*Galantamine and memantine produce different degrees of neuroprotection in rat hippocampal slices subjected to oxygen-glucose deprivation*, M. Sobrado et al., *Neurosci. Lett.* 365, 132-136 (2004); *Neuroprotective effects of the new thiadiazolidone NP00111 against oxygen and glucose deprivation in rat hippocampal slices: implication of Erk1/2 and PPARγ receptors*, A O. Rosa et al., *Experimental Neurology* 212, 93-99 (2008)).

The objective of the assay was to determine the neuroprotective effect of the compounds of formula (I) against the lesion caused by OGD in rat hippocampal slices. The lesion was evaluated by measuring the release of LDH into the extracellular medium as an indicator of cell death or by determining cell viability by means of the reduction of the tetrazolium salt MTT to formazan.

Materials and Methods

Male Spague Dawley strain rats (250-325 g) were used. After anaesthesia by means of an intraperitoneal injection of 60 mg/Kg sodium pentobarbital (Euta-Lender®), they were decapitated with a guillotine and the brain was extracted after a craniotomy. The brain was immediately submersed in a dissection solution, a cold (4° C.) modified Krebs-Henseleit solution at pH 7.4, the composition of which is: 120 mM NaCl, 2 mM KCl, 0.5 mM $CaCl_2$, 26 mM $NaHCO_3$, 10 mM $MgSO_4$, 1.18 mM $KH_2PO_4$, 11 mM glucose and 200 mM sucrose, bubbled with 95% $O_2$-5% $CO_2$. The hippocampi were isolated, embedded in 2% low melting point agarose (Sigma-Aldrich), and cut into 350 µm transverse slices in a vibratome (Leica VT1000S).

After the cutting in the vibratome, the slices were transferred to a vial with sucrose-free dissection Krebs solution, bubbled with 95% $O_2$-5% $CO_2$ for 60 minutes (equilibrium period).

After the equilibrating period, the medium was removed and an oxygenated solution (normal Krebs solution (120 mM NaCl, 2 mM KCl, 2 mM $CaCl_2$, 26 mM $NaHCO_3$, 1.19 mM $MgSO_4$, 1.18 mM $KH_2PO_4$ and 11 mM glucose), bubbled with 5% $CO_2$ and 95% $O_2$ for 30 minutes (preincubation period), was introduced. The baseline slices were maintained in this oxygenated solution throughout the entire experiment. To induce OGD, the oxygenated solution was replaced with another one which lacked glucose and was bubbled with a mixture of gases of 5% $CO_2$ and 95% $N_2$ (anoxic solution). The slices were in a bath at 37° C. After inducing OGD, the anoxic medium was replaced with another one which contained the oxygenated solution (reoxygenation period).

To evaluate the effect of the compounds, they were incubated for the 30 minutes of the preincubation and throughout the OGD and during the reoxygenation. Two OGD-reoxygenation protocols were used: (i) 1 hour of OGD and 2 hours of reoxygenation and (ii) 15 minutes of OGD followed by 2 hours of reoxygenation.

When the OGD-reoxygenation protocol (i): 1 hour of OGD and 2 hours of reoxygenation was used, the slices were incubated with increasing concentrations of compound Ic (1 and 10 µM). The baseline (slices without compound Ic and without OGD) and the control (slices in the absence of compound Ic and with OGD) were also included in the same study.

When the OGD-reoxygenation protocol (ii): 15 minutes of OGD followed by 2 hours of reoxygenation was used, the slices were incubated with increasing concentrations of compound Ic (0.3 and 1 µM) or with increasing concentrations of compound Ib (1 and 3 µM). In the same study these two compounds of the invention were compared with N-acetylcysteine (NAC) at 10 mM. The baseline (slices in the absence of compound Ic or Ib and of OGD) and the control (slices in the absence of compound Ic or Ib and with OGD) were also included.

For the protocol of 1 hour of OGD followed by 2 hours of reoxygenation, the viability was determined by measuring the release of LDH into the extracellular medium according to the method described in Example 3. The quantification of LDH was performed in samples taken (i) after the preincubation period, (ii) after the hour of OGD and (iii) after each hour of reoxygenation (1 hour and 2 hours).

For the protocol of 15 minutes of OGD followed by 2 hours of reoxygenation, the cell viability was evaluated by means of the tetrazolium salt MTT, which is internalized in those cells which are viable and are therefore capable of reducing the tetrazolium to formazan which is an insoluble and coloured product which is deposited in the cell exterior. To that end, after the experiment had ended, the hippocampal slices were incubated with MTT at a final concentration of 0.5 mg/mL in a Krebs-HEPES solution (in mM: NaCl, 144; KCl, 5.9; $MgCl_2$, 1.2; $CaCl_2$, 2; HEPES, 10; glucose, 11; at pH 7.3) at 37° C. After 3 hours, the medium was removed and the formazan precipitated in the solution was dissolved in dimethylsulfoxide. Then, the absorbance was measured in a plate reader (Labsystems iEMS Reader MF), at 500 nm. The data were represented taking the result of the baseline slices, i.e., those not subjected to OGD, as 100% viability.

Results

Figure 4:
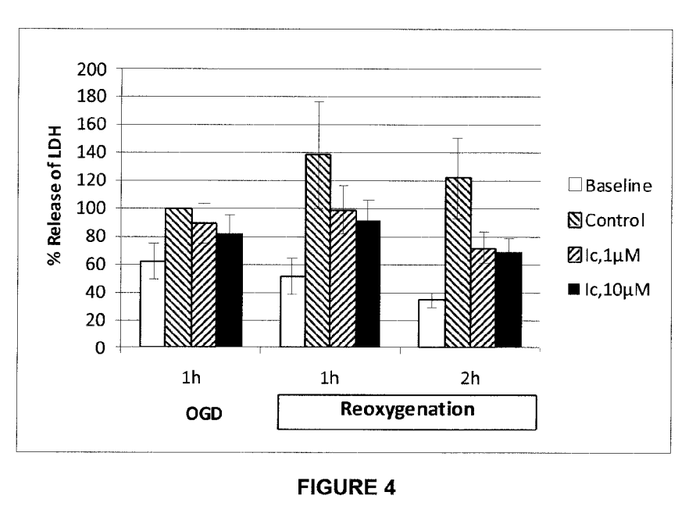
FIG. 4 also depicts, at two concentrations (1 and 10 μM), the effect of compound Ic on the release of LDH into the extracellular medium as an indicator of cell death in rat hippocampal slices subjected to one hour of oxygen and glucose deprivation (OGD) and two hours of reoxygenation. The baseline (slices without compound Ic and without OGD) and the control (slices in the absence of compound Ic and with OGD) are also included.

FIG. 4 shows that compound Ic reduced cell death in a concentration-dependent after one hour of OGD followed by 2 hours of reoxygenation. Although a protective effect of compound Ic against OGD was observed, the protective effect was greater during the reoxygenation stage. At 2 hours of reoxygenation and at the concentration of 1 µM, compound Ic presented a statistically significant protective effect of 40%.

Figure 5:
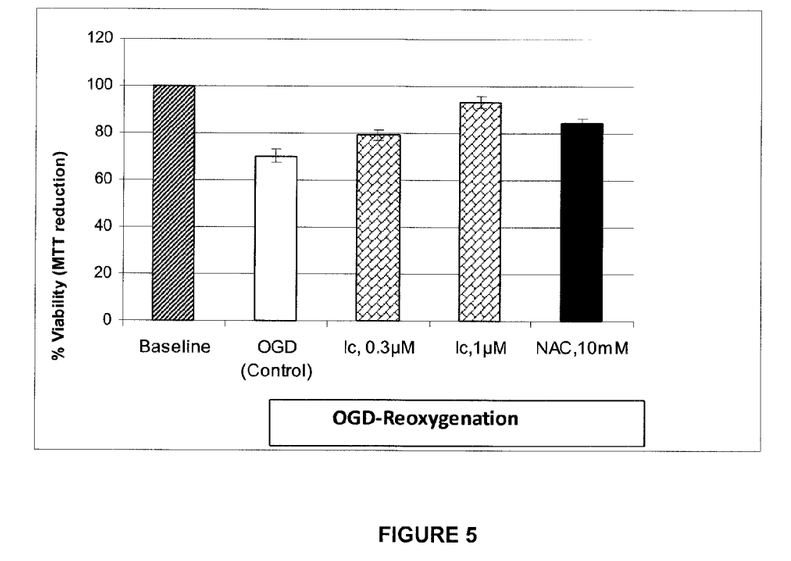
FIG. 5 depicts, at two concentrations (0.3 and 1 μM), the effect of the compound Ic on cell viability (quantified by means of MTT reduction) in rat hippocampal slices subjected to 15 minutes of OGD and two hours of reoxygenation. The effect of compound Ic was compared with the effect of N-acetylcysteine (NAC) at 10 mM. The baseline (slices in the absence of compound Ic and of OGD) and the control (slices in the absence of compound Ic and with OGD) are also included.
Figure 6:
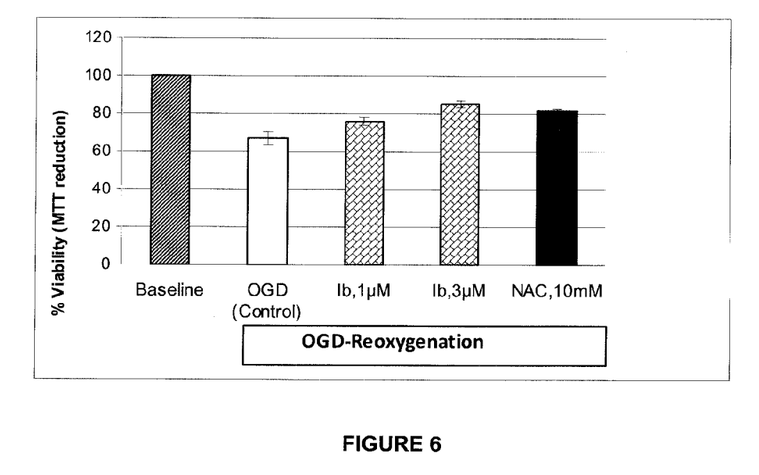
FIG. 6 depicts, at two concentrations (1 and 3 µM), the effect of compound Ib on cell viability (quantified by means of MTT reduction) in rat hippocampal slices subjected to 15 minutes of OGD and two hours of reoxygenation. The effect of compound Ib was compared with the effect of N-acetylcysteine at 10 mM. The baseline (slices in the absence of compound Ib and of OGD) and the control (slices in the absence of compound Ib and with OGD) are also included.

FIGS. 5 and 6 show that in the protocol of 15 minutes of OGD followed by 2 hours of reoxygenation, the OGD-reoxygenation reduced cell viability from 100% (Baseline) to 67% (Control) and that the two compounds Ic and Ib were capable of offering protection.

Compound Ib showed the maximum statistically significant protection (85%) at the concentration of 3 µM, whereas compound Ic was more potent, showing the maximum statistically significant protection (93%) at a concentration of 1 µM.

FIGS. 5 and 6 also show the higher efficacy of compounds Ic and Ib in comparison with N-acetylcysteine, which presented the maximum statistically significant protection (83%) at a millimolar range concentration (10 mM).

Example 6

Anti-Inflammatory Effect of the Compounds of Formula (I) in Lipopolysaccharide (LPS)-Activated Rat Cerebral Cortex Astrocytes Inflammation in the nervous system, known as neuroinflammation, has a different behaviour from that which is manifested in the rest of the organism, mainly due to the presence of inflammatory cells typical of brain tissue.

A neuroinflammatory component is found in some neurodegenerative and neurovascular diseases, so the objective of the present study was to determine if the compounds of the present invention were capable of reducing the release of inflammatory markers by the astroglia.

Materials and Methods

Newborn male rats aged 2-3 days were used. After a craniotomy, both cortices were extracted and deposited in a Petri dish with cold PBS. Under a microscope magnifying lens, the meninges of each cortex were extracted. Once clean, they were submersed in cold DMEM and a mechanical dissection was performed with a pipette. Then, the sample was centrifuged at 1,000 rpm for 5 minutes and the supernatant was decanted. The precipitate was resuspended in DMEM with 20% FBS and a mixture of antibiotics (penicillin/streptomycin). Finally, it was passed through a 70 µm filter and seeded in a 75 $cm^2$ flask with an aerated filter stopper. The calculation for the seeding of the cells was one flask (15 mL of medium) for every newborn used.

The culture medium was replaced after 3 days with a DMEM with 10% serum and the same antibiotics. After one week, 4 µM of ARAC (cytosine arabinoside) was added to each flask to remove the microglia in the culture.

After 3 days of incubation with this cell growth inhibitor, the flasks were stirred at a speed of 250 rpm in a horizontal stirrer inside an oven at 37° C. After 3 hours, the medium was removed from them and it was replaced with a 1:5 mixture of trypsin (0.25% EDTA) PBS. When the medium was removed, the microglia detached with the stirring were removed.

Then, they were left for a few minutes at 37° C. for the trypsin to act. During this time, the astrocytes were observed under the microscope and when they adopted a round shape, or were detached, a 1:5 mixture of FBS/PBS was added to them to block the enzymatic effects of the trypsin.

Subsequently, the medium of each flask was collected and taken to 50 mL Falcon tubes, they were centrifuged for 5 minutes at 1,000 rpm and the supernatant was decanted. The precipitate was resuspended in DMEM with 10% FBS and antibiotics and the cells were counted for their subsequent seeding.

The induction of inflammation in the astrocytes was performed by means of adding 10 µg/mL lipopolysaccharide together with the compounds to be studied (compound Ic at 0.03 µM and chondroitin sulphate at 10 µM) for 2 hours. Then, the RNA of the astrocytes was extracted by the phenol method, with the entire material free of RNAse. The quantification was performed by the direct measurement of absorbance at 260/280 nm in a Nanodrop® spectrophotometer. The amplification of 500 ng of RNA was performed by reverse transcription (5 minutes at 65° C., reverse transcriptase was added to it, 10 minutes at 25° C., 50 minutes at 50° C. and 5 minutes at 85° C.), taking it to a final volume of 15.20 µL.

To conduct the RT-PCR (Reverse Transcription Polymerase Chain Reaction) analysis, an MyiQ5 iCycler system (Bio-Rad Laboratories, Inc., Hercules, Calif.) was used. The thermal annealing conditions were as follows: the initial denaturation at 95° C. for 3 minutes, followed by 40 cycles of 95° C. for 15 seconds and 60° C. for 1 minute. Fluorescence measurements were taken for each annealing step. At the end of each PCR, the data were automatically analyzed by the system and amplification graphs were obtained. For each PCR, 3 µL of template cDNA were added, which was added to 12 µL of IQ™ SYBR-Green Supermix 2×(Bio-Rad) and to which there were added the F and R oligomers for TNF-alpha, IP-10, SOCS, and actin, which was used to prepare the RT-PCR standard curves. All the amplification reactions were carried out in duplicate, and the number of duplicates of the mean threshold cycle ($C_t$) was used to calculate the expression level (number of copies) of the cytokines, using the curve generated by actin as the standard.

The activity of compound Ic was compared with chondroitin sulphate in the same study. The baseline (in the absence of compound and of LPS) and the control (in the absence of compound and with LPS) were also included.

Results

Figure 7:
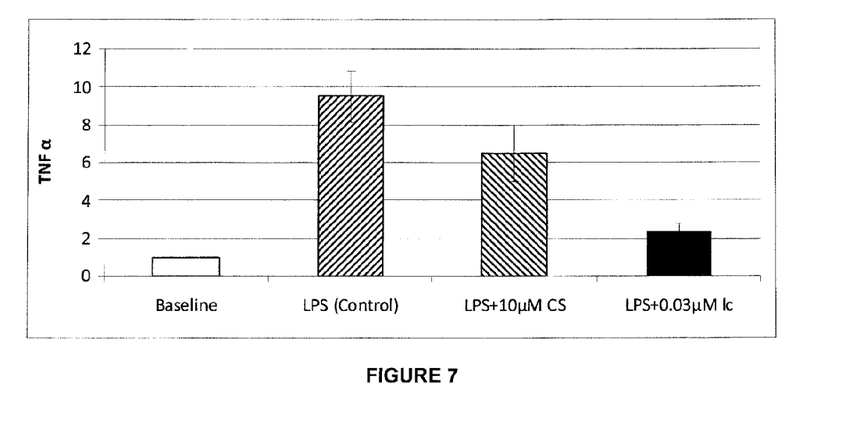
FIG. 7 depicts the effect of compound Ic (0.03 µM) on TNFα production after exposing the rat cerebral cortex astrocytes (incubated with compound Ic) to lipopolysaccharide (LPS) for two hours. The effect of compound Ic was compared with the effect of chondroitin sulphate at 10 µM. The baseline (cells in the absence of compound Ic and LPS) and the control (cells in the absence of compound Ic and in the presence of LPS) are also included.

FIG. 7 shows the anti-inflammatory effect of compound Ic and of chondroitin sulphate in LPS-activated rat astrocytes.

When the rat astrocytes were activated with LPS for 2 hours, there was an increase in the production of TNFα of almost ten times with respect to the baseline (Control bar).

The treatment of the astrocytes, in a simultaneous manner, with LPS and with chondroitin sulphate (10 μM) or with compound Ic (0.03 μM) significantly reduced the production of TNFα, the reduction being greater in the astrocytes treated with Ic (75%) than with chondroitin sulphate (31%).

Example 7

Neuroprotective Effect of the Compounds of Formula (I) in an Experimental Thrombotic Stroke Model in Mice Neuronal death occurs during brain ischemia or stroke; therefore a medicament with a neuroprotective profile can have a therapeutic potential in patients who have suffered from a cerebral infarction or stroke. To explore if the compounds of formula (I) can offer neuroprotection in vivo, the experimental photothrombotic stroke model was used. In the photothrombosis model a focal cerebral infarction is induced in the area of the cortex illuminated by means of a cold light source in mice previously treated with the Rose Bengal stain; this stain is photosensitive and produces free radicals when it is stimulated with light, causing lesions in the surrounding vascular endothelium, which causes platelet aggregation and the formation of thrombi in the microvessels of the cerebral cortex (*Non-invasive induction of focal cerebral ischemia in mice by photothrombosis of cortical microvessels: characterization of inflammatory responses*, M. Schroeter et al., *J Neurosci Methods*. 117(1), 43-49. (2002); *Melatonin reduces infarction volume in a photothrombotic stroke model in the wild-type but not cyclooxygenase*-1-*gene knockout mice*, L Y. Zhou et al., *J Pineal Res*. 41(2), 150-156. (2006)).

Materials and Methods

Adult male Swiss breed mice from Harlan laboratories (Barcelona), with a weight of about 30 g, were used. Once anaesthetised with isoflurane, the mice were placed in a stereotaxic frame, maintaining their rectal temperature at 37±0.5° C. during the entire procedure. Subsequently, the cranium was exposed by means of a dorsomedial incision in the skin and the periosteum was removed. By means of the use of a micromanipulator, a fibre-optic cable was placed to emit a beam of light of 1.9 mm in diameter and 3000° K, connected to a cold light source (Zeiss KL 1500), in 2.0 mm posterior and 3.0 mm lateral to Bregma on the right side. According to the mouse brain atlas (Franklin and Paxinos, 1986), the sensitive-motor cortex, the putamen caudate and the hippocampus are right below this stereotaxic position. Then, the mice were injected with 1 mg of the Rose Bengal photosensitive probe and the brain was illuminated through the intact cranium for 30 minutes. Finally, the skin was sutured and the animals were left in a cage until their recovery under observation.

The animals were sacrificed by decapitation 72 hours after the ischemia. Then, the brains were extracted, cut into 1 mm thick slices (Brain matrix, Stoelting, Wood Dale, Ill., USA), stained with the tetrazolium salt TTC at 2% and fixed by immersion in 4% paraformaldehyde.

To quantify the cortical cerebral infarction volume, the sections stained with TTC were scanned on both their rostral and caudal part and by means of the image analysis programme ImageJ 1.41 (National Institutes of Health, Bethesda, Md., USA) the area of the ipsi-, contralateral cortex and the cerebral infarction of each of the sections scanned, both in the caudal and rostral part, was quantified. Subsequently, the cerebral infarction volume was calculated.

Protocol of Administration of Compound Ic

A dose of 10 mg/kg of compound Ic was used and melatonin at a concentration of 15 mg/kg was used as a positive control as described by L Y. Zhou et al. (*J Pineal Res*. 41(2), 150-156. (2006)). The controls were treated with saline. The different treatments were administered by intraperitoneal (i.p.) route. Compound Ic was administered 24 hours and 1 hour before inducing the brain ischemia. After the induction of the ischemia, the animals were treated by i.p. route twice a day until their sacrifice, 72 hours after the ischemia.

Results

Figure 8:
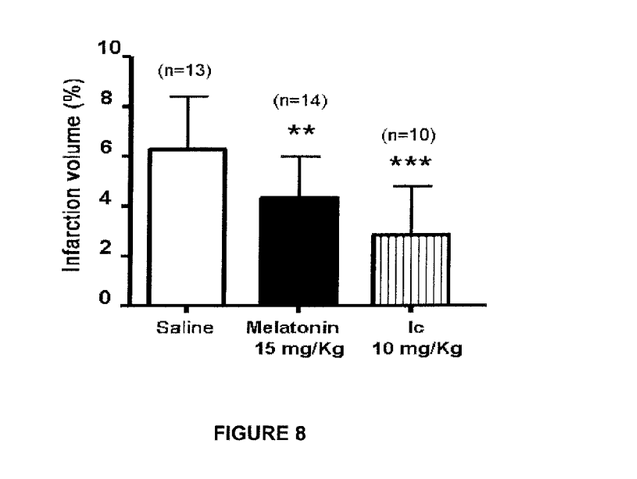
FIG. 8 depicts the reduction of the cortical infarction volume, expressed in percentage, in the animals treated with 10 mg/kg of compound Ic. The effect of compound Ic was compared with the effect of melatonin at 15 mg/kg. The data represent the mean and the standard deviation of the number of animals which are shown in the parentheses above each bar of the figure. p<0.05 and *p<0.001, with respect to the animals treated with saline.

As can be observed in FIG. 8, in the animals treated with saline, the cortical infarction volume induced by photothrombosis was 6.1±2.18%; said cerebral infarction was significantly reduced in the animals treated with 10 mg/kg of compound Ic (2.8±1.95%). Melatonin, which was used as a positive control, caused a significant reduction of the infarction volume (4.3±1.63%). With the expression of these data in terms of protection, compound Ic at the dose of 10 mg/kg provided a 53% protection (p<0.001), whereas melatonin, at the dose of 15 mg/kg, provided a 29% protection (p<0.05).

These results indicate that the compounds of the present invention can be useful in the treatment of cerebral infarction or stroke.

The invention claimed is:

1. A method for the treatment of a neurodegenerative and/or neurovascular disease, in a mammal, comprising administering to a mammal in need thereof an effective amount of a compound of formula (I), wherein:
R$^1$ is selected from hydrogen, linear or branched C$_1$-C$_4$ alkyl, phenylalkyl of less than ten carbon atoms and —COCH$_3$;
R$^2$ is selected from hydrogen, —COCH$_3$ and —SO$_3$Y;
R$^3$ is selected from hydrogen, linear or branched C$_1$-C$_4$ alkyl, phenylalkyl of less than ten carbon atoms, —COCH$_3$ and —COPh, wherein Ph is phenyl;
G is selected from —COOR$^4$ and —COOY;
one of A or B is selected from hydrogen, —SO$_3$H, —SO$_3$Y and —COCH$_3$, and the other
A or B is —SO$_3$H or —SO$_3$Y;
R$^4$ is selected from hydrogen, C$_1$-C$_2$ alkyl and arylalkyl of less than sixteen carbon atoms,
Y is an organic or inorganic cation;
or a pharmaceutically acceptable salt thereof; wherein the neurodegenerative and/or neurovascular disease is selected from the group consisting of Alzheimer's disease, Parkinson's disease, amyotrophic lateral sclerosis, multiple sclerosis, stroke, transient ischemic brain attack, Huntington's disease, Friedreich's ataxia, spongiform encephalopathies, dementia with Lewy bodies, Pick's disease, mild cognitive impairment, epilepsy, migraine, schizophrenia, bipolar disorder, vascular dementia and cerebrovascular arteriosclerosis.

2. The method according to claim 1, wherein $R^1$ is selected from hydrogen and linear $C_1$-$C_4$ alkyl and G is selected from —COOR$^4$ and —COOY, wherein $R^4$ is hydrogen or $C_1$-$C_2$ alkyl and Y is an inorganic cation.

3. The method according to claim 2, wherein $R^1$ is hydrogen, $R^2$ is —COCH$_3$ and $R^3$ is hydrogen.

4. The method according to claim 2, wherein $R^1$ is methyl, $R^2$ is —COCH$_3$ and $R^3$ is hydrogen.

5. The method according to claim 3 or claim 4, wherein A is hydrogen, B is
   —SO$_3$Y and G is —COOY, wherein Y is an inorganic cation.

6. The method according to claim 3 or claim 4, wherein A is —SO$_3$Y, B is hydrogen and G is —COOY, wherein Y is an inorganic cation.

7. The method according to claim 3 or claim 4, wherein A and B are —SO$_3$Y and G is —COOY, wherein Y is an inorganic cation.

8. The method according to claim 4, wherein the compound of formula (I) is selected from the group consisting of:

and

9. The method according to claim 7, wherein the compound of formula (I) is:

10. The method according to claim 1 or claim 8, wherein the neurodegenerative and/or neurovascular disease is associated with oxidative stress.

11. The method according to claim 1 or claim 8, wherein the disease is Alzheimer's disease.

12. The method-according to claim 1 or claim 8, wherein the disease is Parkinson's disease.

13. The method according to claim 1 or claim 8, wherein the disease is amyotrophic lateral sclerosis.

14. The method-according to claim 1 or claim 8, wherein the disease is stroke.

15. A method for the treatment of an oxidation-associated neurodegenerative and/or neurovascular disease, comprising administering to a mammal in need thereof an effective amount of a compound of formula (I)

wherein:
   $R^1$ is selected from hydrogen, linear or branched $C_1$-$C_4$ alkyl, phenylalkyl of less than ten carbon atoms and —COCH$_3$;
   $R^2$ is selected from hydrogen, —COCH$_3$ and —SO$_3$Y;
   $R^3$ is selected from hydrogen, linear or branched $C_1$-$C_4$ alkyl, phenylalkyl of less than ten carbon atoms, —COCH$_3$ and —COPh, wherein Ph is phenyl;
   G is selected from —COOR$^4$ and —COOY;
   one of A or B is selected from hydrogen, —SO$_3$H, —SO$_3$Y and —COCH$_3$, and the other A or B is —SO$_3$H or —SO$_3$Y;
   $R^4$ is selected from hydrogen, $C_1$-$C_2$ alkyl and arylalkyl of less than sixteen carbon atoms,
   Y is an organic or inorganic cation;
   or a pharmaceutically acceptable salt thereof;
      wherein the oxidation-associated neurodegenerative and/or neurovascular disease is selected from the group consisting of Alzheimer's Disease, Parkinson's Disease, amyotrophic lateral sclerosis, multiple sclerosis, stroke, transient ischemic brain attack, Huntington's disease, Friedreich's ataxia, spongiform encephalopathies, dementia with Lewy bodies, Pick's disease, mild cognitive impairment, epilepsy, migraine, schizophrenia, bipolar disorder, vascular dementia and cerebrovascular arteriosclerosis.

16. The method according to claim 15, wherein the compound of formula (I) is selected from a group consisting of:

and

17. The method according to claim 16, wherein the compound of formula (I) is: